United States Patent [19]

Tiholiz et al.

[11] Patent Number: 5,036,733
[45] Date of Patent: Aug. 6, 1991

[54] CO-APTIVE INSTRUMENTS WITH NON-SLIP SURFACES AND METHOD FOR THEIR MANUFACTURE

[76] Inventors: Ivan C. Tiholiz, 10421 Beckford, Northridge, Calif. 91326; William J. Ogden, 22620 Gilmore, West Hills, Calif. 91307

[21] Appl. No.: 387,656

[22] Filed: Jul. 31, 1989

Related U.S. Application Data

[63] Continuation-in-part of Ser. No. 180,437, Apr. 12, 1988, abandoned.

[51] Int. Cl.⁵ .......................... B21K 5/00; B25B 7/02
[52] U.S. Cl. ................................. 76/119; 76/DIG. 12
[58] Field of Search .............................. 606/205–207, 606/210, 131; 294/99.5; 81/9.22, 100, 418; 76/101.1, 119, DIG. 12; 51/293, 295

[56] References Cited

U.S. PATENT DOCUMENTS

| | | | |
|---|---|---|---|
| 2,743,726 | 5/1956 | Grieshaber | 128/322 |
| 3,273,933 | 9/1966 | Jochim | 81/418 |
| 3,957,298 | 5/1976 | Purchase | 294/99.2 |
| 4,778,730 | 10/1988 | Zucker | 81/900 |

FOREIGN PATENT DOCUMENTS

| | | | |
|---|---|---|---|
| 0571738 | 9/1945 | United Kingdom . | |
| 0831750 | 3/1960 | United Kingdom . | |
| 2063743 | 6/1981 | United Kingdom | 81/900 |
| 2086792 | 5/1982 | United Kingdom | 128/321 |

OTHER PUBLICATIONS

Ross, J. Cosbie, "New Inventions: Diathermy Hemostats for Prostatectolmy", The Lancet, Feb. 11, 1956, p. 268.

*Primary Examiner*—Roscoe V. Parker
*Attorney, Agent, or Firm*—Edward A. Sokolski

[57] ABSTRACT

A co-aptive surgical instrument has a pair of opposite facing co-aptive surfaces for grasping tissue. The co-aptive surfaces are formed with a matrix layer which is preferably of a metal such as nickel with a plurality of hard crystalline particles which are preferably a diamond grit which is captured in the matrix. To insure sufficient capture of the particles in the matrix so as to avoid loss of particles while at the same time providing the maximum possible protrusion of the particles and maximum coverage of the surface by such particles, the particles are oriented in juxtaposition to evenly cover the surface and the matrix is made to have a depth which is at least fifty percent of the average diameter of the particles.

4 Claims, 6 Drawing Sheets

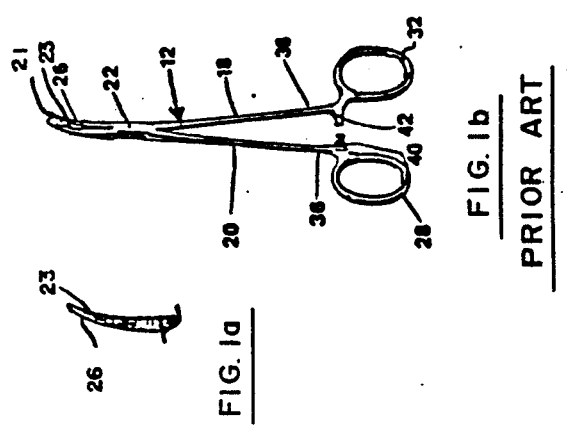
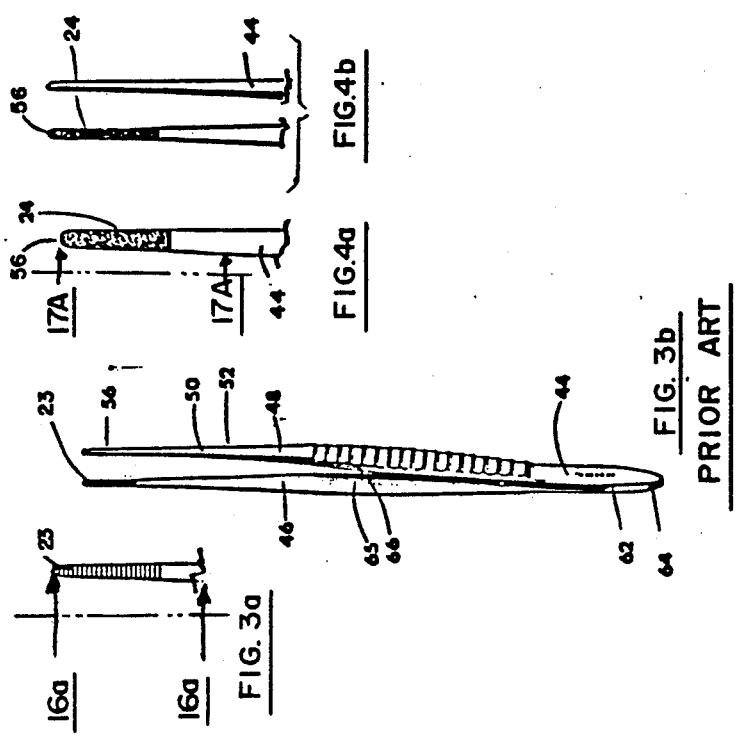
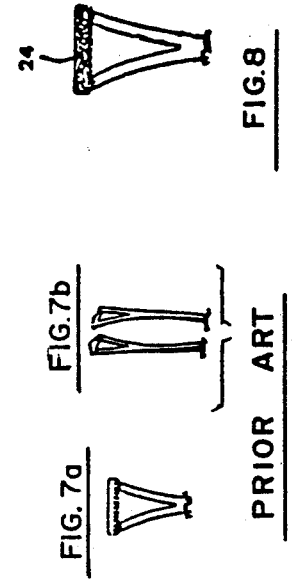
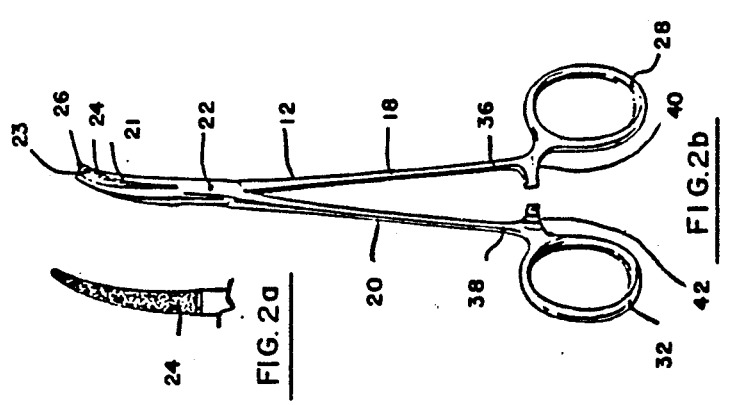
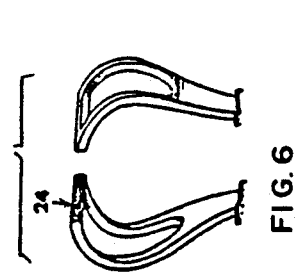
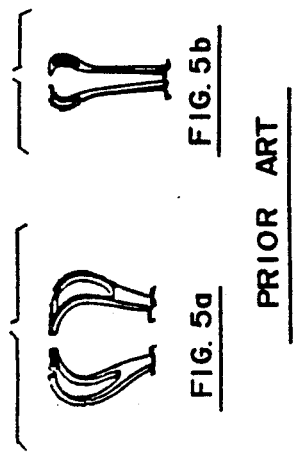

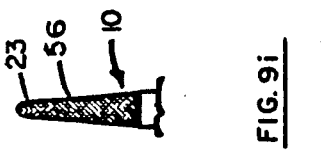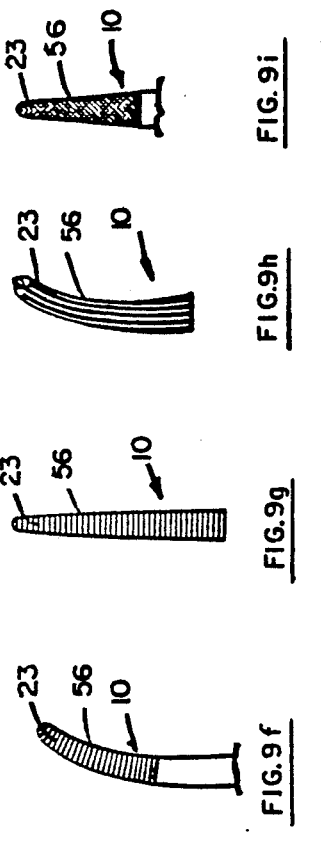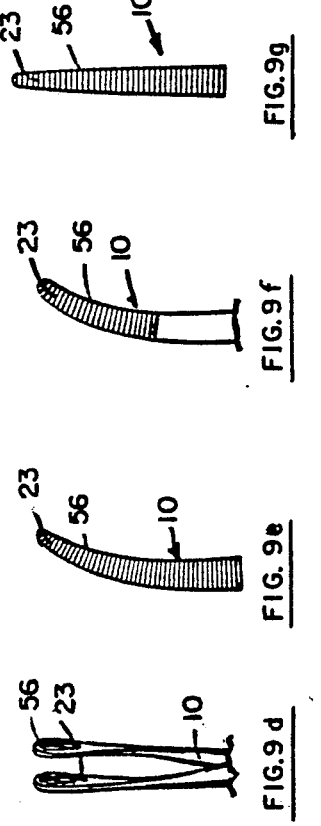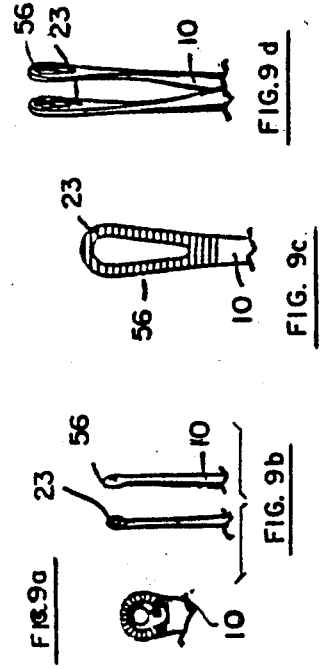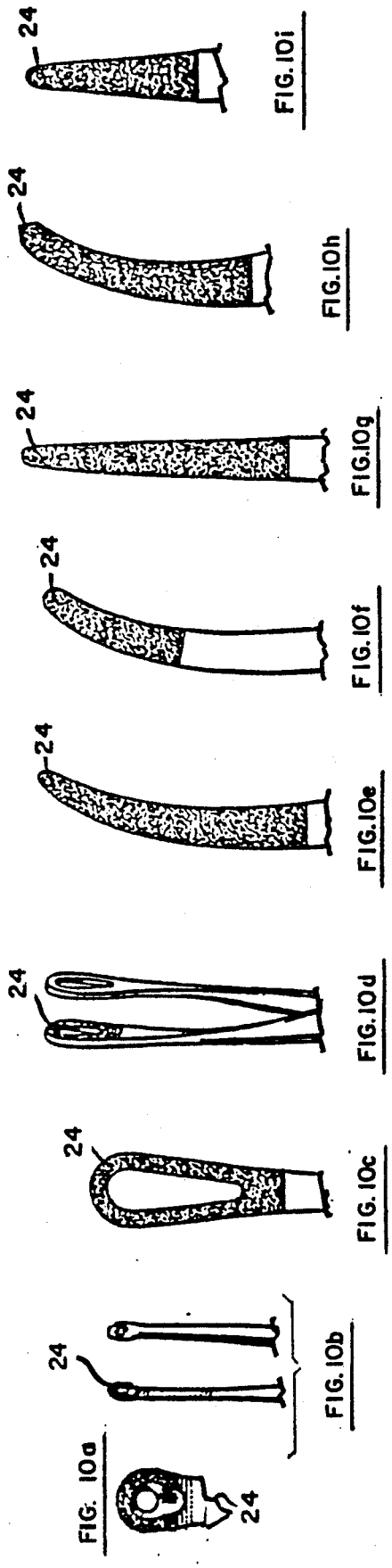

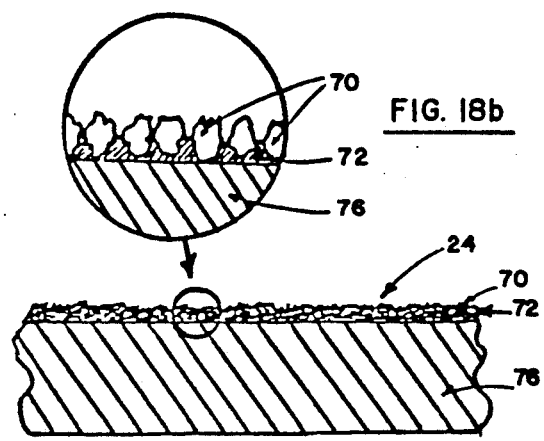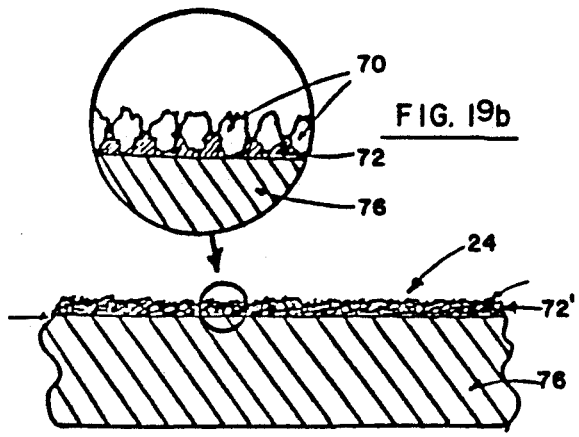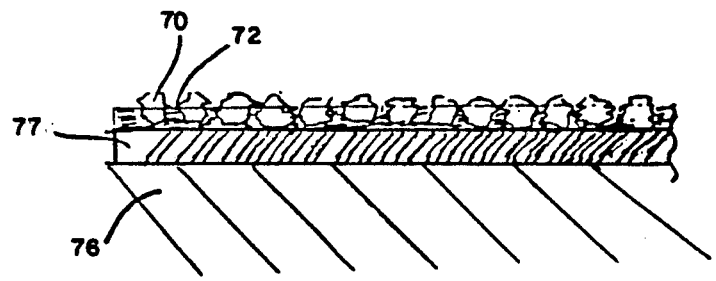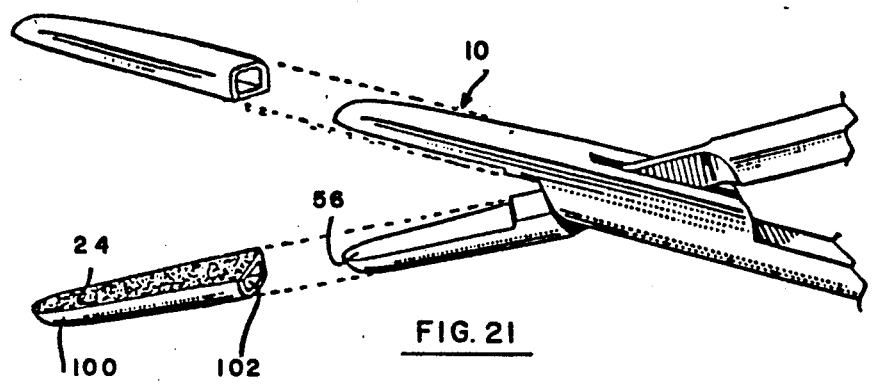

CO-APTIVE INSTRUMENTS WITH NON-SLIP SURFACES AND METHOD FOR THEIR MANUFACTURE

BACKGROUND OF THE INVENTION

This application is a continuation in part of our application Ser. No. 180,437 filed Apr. 12, 1988 now abandoned.

This invention relates generally to medical instruments and, more specifically, to co-aptive instruments having non-slip, engaging surfaces, which may be electrically conductive, formed of hard crystalline particles, for example, diamond, silicon carbide, and/or aluminum oxide grit, suspended in a suitable matrix.

There are a multitude of instruments which are used to grasp other tools or pieces of body tissue between a pair of engaging surfaces, e.g., forcepts, clamps, and hemostats. Generally, these instruments may be used to grasp other instruments, e.g., needles or electrodes, or to clamp separate pieces of animal tissue together so that the tissue may be sutured or otherwise more permanently joined. Alternatively, these instruments may be used to clamp or to grasp and otherwise manipulate tissue to enable easier access to adjacent tissues or organs.

Since most items grasped during surgical procedures are typically moist and slipper, the item may slip from the co-aptive instrument'grasp. Responsive to this problem, one solution includes the application of engaging surfaces; see U.S. Pat. No. 2,755,806, issued July 24, 1956 to E. M. Green berg; and U.S. Pat. No. 4,315,447, issued Feb. 16, 1982, to L. Tartaglia, et al. However, recent developments in the medical and surgical arts may call for electro-stimulation or electrical monitoring of the grasped tissue. Conventional coatings of non-slip materials which may improve the grip of the engaging surface may not conduct electrical impulses, thereby preventing such desired monitoring or stimulation of the gasped tissue.

An electroconductive engaging surface, i.e., a metallic or metallized one, may be serrated or cross-hatched. This increases the roughness of the surface and, therefore, the grasping friction. However, these serrations or cross-hatchings may not provide an adequate number of contact points on the co-aptive surface to adequately reduce slippage. Generally, serrations or cross-hatchings are a series of substantially parallel and linear alternating ridges and grooves formed in the engaging surface. This serrated surface may be formed by inscribing, e.g., with a rotary saw or grinding wheel, or by casting, knurling, or other state-of-the art machining methods. As a result, there is an upper limit to the number of cross-hatching which can be practicably formed within the engaging surface, as determined by the width of the inscribing implement and the precision and resolution of the inscribing machine. Another limiting factor is the need to blunt or round each ridge's apex. Increasing the number of ridges per inch concurrently decreases the width of each ridge. A thin, sharp-edged apex may, under applied pressure, either fail mechanically, or cut or injure the item grasped between the jaws. Furthermore, since the serrations or cross-hatching are generally linear, needles or other generally rectilinear instruments grasped by the co-aptive tools may fall within one of the inscribed grooves. As a result, under the intense rotational force which is exerted during suturing, the needle may roll about its longitudinal axis because of an insufficient number of contact points. Moreover, merely increasing the compression exerted by the opposing jaws upon the grasped item may be limited by the strength of the tool or the operator, or, even worse, cause damage, fracturing, breaking or peeling to the needle itself. This needle failure, in turn, may result in the deposition of microscopic or larger metallic fragments in the tissue or organs.

Hence, those concerned with the development of co-aptive medical instruments have long recognized the need for improvements in such instruments which provide an extremely large number of holding points within the engaging surface area for enhanced gripping, while minimizing the damage to the instrument or tissue held between the opposing engaging surfaces. The non-slip surface may also be capable of conducting electrical current to, or impulses from, the grasped item. In addition, there is a need for co-aptive instruments, or fragments therefrom, which, if inadvertently left within the patient, will not cause suppuration, i.e., do not induce foreign body reaction if left in situ.

Gripping tools and forceps which employ gripping surfaces formed by embedding diamond or other such hard crystalline granules in a matrix which may be metallic are described in U.S. Pat. No. 3,273,933 to Jochim, British Pat. No. 571,738 to Keeleric, and British Pat. No. 831,750 to Drendel. While employing similar basic structure similar to that of the present invention, none of these prior art patents describes such a device which has the characteristics necessary to make for a high quality co-aptive medical instrument with non slip engaging surfaces which provide good holding action without damaging either the surfaces being held or the instrument itself.

SUMMARY OF THE INVENTION

Briefly, and in general terms, the present invention provides a new and improved apparatus and method for its manufacture which enhances, by orders of magnitude, the gripping friction of a co-aptive instrument while minimizing the damage to the item being held by the apparatus.

Basically, the present invention is directed to a new and improved co-aptive instrument with a variety increased number of contact points maintaining a grip on an item being held by the apparatus. In accordance with the invention, one embodiment includes an apparatus having a pair of substantially opposite-facing engaging surfaces, with an electrically conductive deposit including a particulate grit as a means for engaging and electrically contacting the item or material between the surfaces. The grip includes numerous discrete particles partially embedded in the engaging surfaces, increasing by order of magnitude the number of contact points, and thus the gripping friction of the engaging surface, without a sacrifice in electrical conductivity.

The desired end results are achieved in the present invention in the following manner:
1. The crystalline particles are randomly distributed in an even manner over the co-aptive surface which avoids gaps and voids therein.
2. Maximum protrusion of the crystalline particles is provided to ensure proper co-aptivity while at the same time providing sufficient capture in the matrix to avoid loss of particles.

3. Particles having sharp blocky shapes are employed to assure maximum packing density and allowing 100% of the surface to be co-aptive.
4. The particle size and matrix depth are controlled to assure maximum co-aptivity.

The device and method of the present invention are directed towards achieving the above indicated end results, making for a surgical instrument having significantly improved characteristics as compared with prior art devices.

In the illustrative embodiment of the invention, which is disclosed by way of example and not necessarily by way of limitation, hard crystalline particles are partially embedded within an electrically conductive nickel alloy matrix. The metallic matrix is electrodeposited or electroplated upon the surface. These improved co-aptive instruments have engaging surfaces which are electrically conductive and have a greater gripping friction without applying additional damaging compressive pressure to the items grasped.

These and other objects and advantages of the invention will become apparent from the following more detailed description, when taken in conjunction with the accompanying drawings of illustrative embodiments.

DESCRIPTION OF THE DRAWINGS

FIG. 1a is a fragmentary, plan view of a prior art co-aptive surface;

FIG. 1b is a reduced, perspective view of a prior art co-aptive instrument;

FIG. 2a is an enlarged, fragmentary plan view of a co-aptive surface incorporating the novel features of the present invention;

FIG. 2b is an enlarged, perspective view of a co-aptive instrument incorporating the novel features of the present invention;

FIG. 3a is an enlarged, fragmentary plan view of a prior art co-aptive surface;

FIG. 3b is a perspective view of another embodiment of a prior art co-aptive instrument;

FIG. 4a is an enlarged, fragmentary perspective view of yet another embodiment of a co-aptive surface of the present invention;

FIG. 4b is an enlarged, fragmentary perspective view of yet another embodiment of the present invention;

FIG. 5a is a fragmentary perspective view of still another prior art co-aptive instrument;

FIG. 5b is a reduced fragmentary perspective view of still another prior art co-aptive instrument;

FIG. 6 is an enlarged, fragmentary view of yet another embodiment of the present invention;

FIG. 7a is a fragmentary, plan view of yet another embodiment of a prior art co-aptive instrument;

FIG. 7b is a fragmentary, perspective view of another embodiment of a prior art co-aptive instrument;

FIG. 8 is an enlarged, fragmentary plan view of another embodiment of the present invention;

FIGS. 9a,c, and e–i are fragmentary, plan views of the grasping end of additional embodiments of prior art co-aptive instruments;

FIGS. 9b and 9d are fragmentary, perspective views of prior art co-aptive instruments;

FIGS. 10a,c and e–i are enlarged, fragmentary plan views of still additional embodiments of the present invention;

FIGS. 10b and 10d are enlarged, fragmentary perspective view of the co-aptive surfaces of the present invention;

FIG. 11b is a fragmentary, plan view of the co-aptive surface of the needle-holding instrument of FIG. 11a;

FIG. 12b is an enlarged, fragmentary plan view of a co-aptive surface of the instrument of FIG. 12a;

FIG. 13b is an enlarged, fragmentary plan view of the co-aptive surface of the embodiment of FIG. 13a;

FIG. 14b is a plan view of the co-aptive surfaces of the embodiment of FIG. 14a;

FIG. 15 is an enlarged cross-sectional view taken substantially along the lines 15—15 of FIG. 14a;

FIG. 16a is an enlarged, fragmentary side elevational, sectional view taken substantially along the lines 16a–16a of FIG. 3a;

FIG. 16b is an enlarged, front elevational, sectional view taken substantially along the lines 16b—16b of FIG. 16a;

FIG. 17a is an enlarged, fragmentary sectional view taken substantially along the liens 17a—17a of FIG. 4a;

FIG. 17b is an enlarged, sectional side elevational view taken substantially of the area circled in FIG. 17a;

FIG. 18a is an enlarged fragmentary sectional side elevational view of another embodiment of the present invention similar to that of FIG. 17a;

FIG. 18b is an enlarged, sectional side elevational view taken substantially of the area circled in FIG. 18a;

FIG. 19a is an enlarged, fragmentary sectional side elevational view of yet another embodiment of the present invention similar to that of FIG. 17a;

FIG. 19b is an enlarged, sectional side elevational view taken substantially of the area circles in FIG. 19a;

FIG. 20 is an enlarged fragmentary sectional view of still another embodiment of the engaging surface of the present invention;

FIG. 21 is an enlarged, fragmentary exploded perspective view of a still further embodiment of the present invention;

DETAILED DESCRIPTION OF THE INVENTION

Figure 11A:
FIG. 11a is a fragmentary, perspective view of a prior art needle-holding instrument.

As shown in the exemplary drawings for the purposes of illustration and not limitation, a co-aptive instrument of the present invention is primarily concerned with an engaging surface having an increased number of contact points for enhancing the gripping friction of the co-aptive tool. The engaging surface may also be electrically conductive.

Referring to FIG. 1b, there is shown a prior art co-aptive instrument. For the purposes of illustration, a hemostat 12 may include needle-holder configurations known in the art as "Crile-wood", "Baumgarter", "Mayo-Heger", "New Orleans" or "Vital French Eye". Generally, the hemostat 12 includes a pair of lever arms 18 and 20 pivotally mounted upon one another about a pin 22. Rotation of the first lever arm 18 about the pin 22 enables a scissoring of the first lever arm 18 relative to the second lever arm 20, enabling jaws 21 having substantially opposite-facing engaging surfaces 23 disposed at a gripping or end tip 26 to selectively move from a first position separated from one another to a second position closely adjacent to one another, into engagement with the material, e.g., tissue or another instrument (not shown) held between the jaws. Generally, handle loops 28 and 32 may be formed in each lever arm 18 and 20 at handle ends 36 and 38, respectively, substantially remote from the engaging surfaces 23. Interlocking tangs 40 and 42 formed adjacent to the handle loops 28 and 32 are positioned and configured to releasably engage one another. These tangs 40 and 42 releasably lock the handle loops 28 and 32 adjacent to one another and thus retain the engaging surfaces 23 of the hemostat instrument 12 in a second or pinching position closely adjacent to one another and grasp the tissue between the engaging surfaces. Generally, as shown in FIG. 1a, the engaging surface 23 is serrated adjacent the tip 26 to enhance the jaw's gripping or frictional coefficient. Throughout the drawings, like reference numerals denote corresponding structural elements having substantially the same or similar characteristics.

There is shown in FIGS. 2a and 2b, an enlargement of the co-aptive instrument 10, e.g., a hemostat 12, incorporating the novel features of the present invention, showing in more detail, the engaging surface 23 including the improved engaging surface 24 which incorporates the novel features of the present invention having an increased number of discrete contact points.

As observed in FIG. 3b, there is shown a pair of prior art forceps 44 to selectively move the inwardly or opposite-facing engaging surfaces 23 from a first position separated from one another to a second position closely adjacent to one another. The forceps 44 include a pair of legs 46 and 48, substantially parallel to each other and having diagonals 50 at a first or grasping end 52. The engaging surfaces 23 are formed adjacent or upon forcep tips 56 extending from the diagonals 50. A spot weld 62, at a handle end 64 remote from the grasping end 52, pivotally mounts the legs 46 and 48 to one another. The legs 46 and 48 are mounted upon each other's corresponding inwardly facing surfaces 65 and 66. The resiliency of the legs 46 and 48 enable the forcep tips 56 to selectively move outward or inward relative to each other to release or grasp the material or other instrument (not shown) between the opposite-facing engaging surface 23. Generally, as shown in FIG. 1b, the engaging surface 23 is serrated adjacent the forcep tips 56 to enhance the jaw's gripping or frictional coefficient.

As best shown in FIGS. 4a and 4b, another embodiment of the present invention includes the engaging surface 23 at the forcep tips 56 as having the improved engaging surface 24 which incorporates the novel features of the present invention. This provides a myriad of discrete contact points formed on the engaging surfaces to vastly increase the number of co-aptive contact points of the co-aptive instrument, e.g., forceps 44.

Of course it will be appreciated that the improved engaging surface 24 may be incorporated in other conventional or prior art co-aptive instruments to grasp wet, slippery tissue or other difficult to grasp objects or instruments. For example, there is shown in FIGS. 5a-b, FIGS. 7a-b, and FIGS. 9a-i, for the purpose of illustration and not limitation, other conventional co-aptive instruments 11, including Adair tissue-holding forceps, Allis tissue-holding forceps, and other co-aptive instruments, having various forms of conventional engaging surfaces 23 formed adjacent the tips 56. Thus, referring now to FIGS. 6, 8 and 10 a-i, the improved co-aptive engaging surface 24 incorporating the novel features of the present invention can be formed upon the engaging surface 23 and used to vastly increases the gripping coefficient of a wide variety of prior art co-aptive instruments to enhance their gripping of wet or slippery materials or other instruments.

Figure 11B:
Figure 12A:
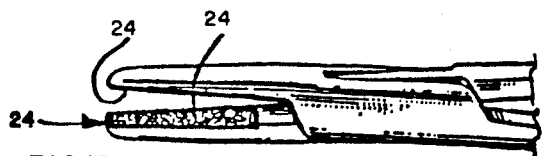
FIG. 12a is an enlarged fragmentary perspective view of needle-holding instrument incorporating the novel features of the present invention.
Figure 12B:

Another embodiment of the present invention provides an increase in gripping coefficient for various forms of prior art needle-holding forceps, as shown in FIGS. 11a and 11b. Referring now to FIGS. 12a-15, there are shown additional embodiments of the co-aptive instruments 10 of the present invention incorporating the engaging surface 24. For example, one embodiment may include the replacement of the conventional cross-hatchings, as shown in FIGS. 11a and 11b, with substantially parallel engaging surfaces 24, as shown in FIGS. 12a and 12b.

Figure 13A:
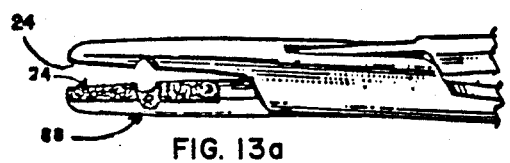
FIG. 13a is an enlarged, fragmentary perspective view of a still further embodiment of the present invention.
Figure 13B:
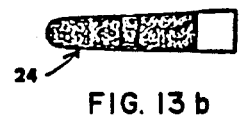

Yet another embodiment of a co-aptive instrument 10 of the present invention is shown in FIGS. 13a and 13b. Parallel grooves 88, which are sized to receive a needle or other rectilinear instrument (not shown) generally orthogonal to the longitudinal axis of the co-aptive instrument, are defined within engaging surfaces 24. The parallel grooves 88 may be sized or machine to have a diameter slightly smaller than that of standard needles, such that the insertion of the needle within such parallel grooves 88, and the juxtaposition of the generally planar engaging surfaces 24 will result in a firm, but minimally compressive, clamping of the needle within the grooves 88. The grooves 88 may also be formed oblique or parallel to the longitudinal axis of the co-aptive instrument. The grooves 88, when the surfaces 24 are juxtaposed, together form a bore which engages a substantial portion of the arcuate peripheral surface of the needle.

Figure 14A:
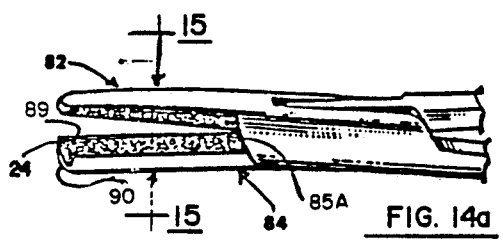
FIG. 14a is a perspective view of another embodiment of the invention.
Figure 14B:
Figure 14C:
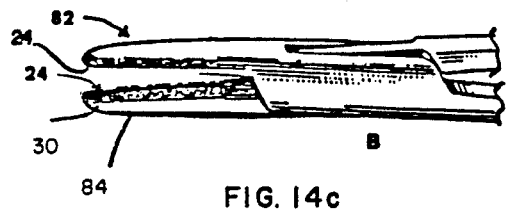
FIG. 14c is an enlarged, fragmentary perspective view of yet another embodiment of the present invention.

There is shown in FIGS. 14a-c and 15 still further embodiments of needle-holding co-aptive instruments 10 embodying the novel features of the present invention. Referring now to FIGS. 14a and 14b, one embodiment of the co-aptive instrument 10 has a first jaw 82 with an outwardly projecting arcuate surface. A second jaw 84 is positioned adjacent the first jaw 82 and has a longitudinal recess 85 which correspond to the outward projection of the first jaw 82. This provides corresponding engaging surfaces 24 which, when juxtaposed, include an increased number of co-aptive contact points formed upon mated arcuate engaging surfaces. In addition, the lower jaw 84 may define an open C-shaped aperture 89 defined within the tip 90 of the second jaw 84. Alternatively, as shown in FIG. 14c, the tip 90 of second jaw 84' may be enclosed.

Figure 15:
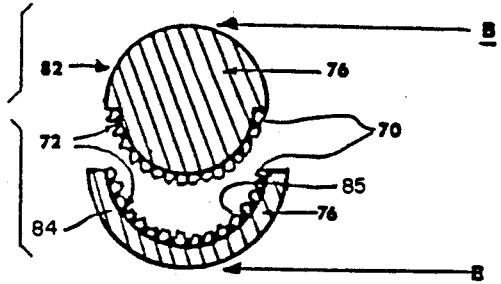

As best shown in FIG. 15, the outward projection of the first jaw 82, is preferably sized to correspond to the depth of the recess 85 of the second jaw 84 such that when the first jaw 82 is moved closely adjacent to the second jaw 84, the arcuate surfaces are closely adjacent one another with a vastly increased number of co-aptive contact points upon the engaging surfaces 24.

While previous embodiments had the improved engaging surface formed directly upon the engaging jaws, FIG. 21 shows a still further embodiment of the present invention. A sleeve 100 having the improved engaging surface 24 formed upon a portion of the exterior and a hollow interior 102 receives and is mounted upon the tip 56 of the co-aptive instrument 10. The sleeves 100 may be fixed in position, for example, by friction, heat shrinking, adhesives or mechanical means, e.g., set-screws or snap rings. The sleeves 100 may be formed of any suitable matrix materials, e.g., metals, elastomers, or thermoplastics. As described in more detail elsewhere in this application, elastomers or thermoplastics can be metallized by vacuum deposition or mixed with graphite fibers to provide the desired conductivity.

Figure 16B:
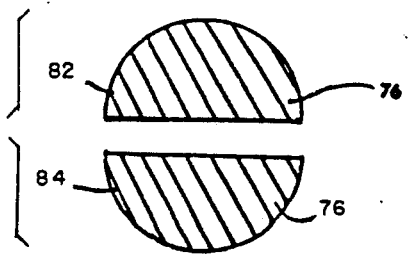
Figure 16A:
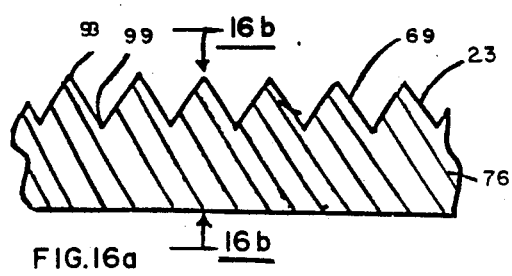
Figure 17B:
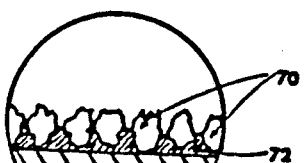
Figure 17A:
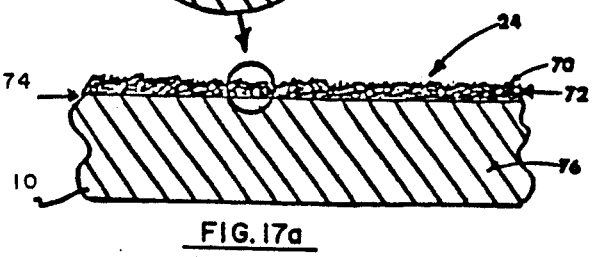

To more fully illustrate the differences between the conventional engaging surfaces 23, as best shown in FIGS. 16a and 16b, with the improved engaging surfaces 24 of the present invention, as shown in FIGS. 17a and 17b, a more detailed description of the respective surfaces is provided.

Referring now to FIG. 16a, there is shown the multiple serrations 69 formed within the engaging surface 23 of the substrate 76, the multiple serrations 69 including a series of alternating ridges 98 and grooves 99, the apices of the ridges 98 of the first jaw 82 generally lying within a single plane. As shown in FIG. 16b, this plane is defined in the exterior surface of the first jaw 82 and is generally parallel to the corresponding plane defined in the engaging surface of the second jaw 84 by the corresponding ridges and grooves formed in that surface. The average density or number of cross-hatchings in the surfaces of conventional tools generally varies between about twelve to thirty-six grooves per inch, yielding about twelve to about thirty-six contact points per square inch of surface area.

As best shown in FIGS. 17a and 17b, the engaging surfaces 24, e.g., the textured outermost surface, may be characterized by hard crystalline grit or particles 70, e.g. silicon carbide, aluminum oxide or diamond particles, partially embedded within a matrix 72, the matrix 45 being formed, e.g., electroplated or electrodeposited, upon an exterior surface 74, e.g., the substrate or main body 76 of the co-aptive instrument 10. Partial embedding is defined as setting or fixing a portion of the particles within the matrix while having other particle portions extend outward uncovered from the surface of the matrix. In one embodiment, the depth of the metallic matrix layer is equal to between 50% to about 60% of the average diameter of the crystalline particles used. This provides a maximum extension of the crystalline particles outward from the matrix while maintaining maximum retentive characteristics of the matrix with a minimized depth. A nickel matrix is preferably used in this embodiment because of its electrochemical properties of low internal stress, ductility, malleability, conductivity and smoothness to secure the grit particles 70.

The substrate 76 of the co-aptive instrument 10 is formed, in one embodiment, of stainless steel and shaped in a conventional manner to function as a hemostat, needle-holder, tissue-holding and forceps or tissue-grasping forceps, as described above.

While co-aptive surfaces with crystalline particles partially embedded within a metallic matrix has been described, other suitable matrices and substrates can be used, e.g., those of FIGS. 18 a-b and 19 -b. For example, referring now to FIGS. 18 a-b, the crystalline particles 70 are partially embedded or melt set within a matrix 72, e.g., nickel plating, adhesive, or elastomer, upon a thermoplastic or resinous substrate, e.g., "LEXAN" or "ULTEM" bran thermoplastics sold by General Electric Company, or "KEL-F" Brand chlorotrifluoropolyethylene by 3-M Corporation of Minneapolis Minn. If a metallic matrix is not used, electrical conductivity may be provided by including carbon fibers or metal powders within the matrices.

Referring now to FIG. 19, hard crystalline particles 70 may be partially embedded and evenly dispersed within the matrix 72', formed of an elastomeric or adhesive material. The elastomeric matrix 72' is mounted upon the substrate 76 by conventional methods, known in the art, e.g., by adhesives, heat or a combination of both. The instrument 10 can then be metalîized by vacuum deposition of gold, by methods well-known in the art, to provide the desired conductivity.

There is shown in FIG. 20, another embodiment of co-aptive instrument 10, which includes a resilient layer 77 of an elastomeric material interposed between the metallic matrix 72 and the stainless steel or thermoplastic substrate 76. The particles 70 are partially embedded in the matrix 72. The incorporation of an elastomeric material provides a cushioned high friction, non-slip and high grip engaging surface which can distribute compressive force over a broader surface area and allow the improved engaging surface to the shape of the material or item grasped between the engaging jaws, increasing the contacted surface area.

Regarding the crystalline particles 70, in one embodiment diamond grit size of about 50 to about 600 U.S. mesh in size is preferred, although any size that is capable of being captured in the matrix may be used. The choice of the grit size is dependent upon the size of the instrument and the application. The larger diamond particles (lower numerical designations) are generally incorporated within co-aptive instruments for use in less fragile applications. While various types of diamond particles may be incorporated in the present invention, the preferred type for medical applications is "Selected natural Diamond Metal Bonds" ("SNDMB") particles available from the Diamond Abrasives Corporation of New York City, N.Y. This type of diamond particle, is observed in FIG. 22, has a myriad number of points and re-entrant angles increasing the number of contact points and enhancing the retention ability of the matrix 72. Furthermore, if any particles should be left in the tissue or organs, the diamond particles, being substantially pure carbon, would be compatible with the human body or in the worst case, inert.

As a result, on one example, of the fixation of the discrete diamond particles partially within the metallic matrix, there is a vastly increased number of contact points per square inch. For example, by using U.S. mesh 140 grit with a mean diamond particle diameter of approximately 0.004 inches, the dispersal of the grit particles would provide an average linear density of contact points equal to approximately 250 per square inch. This would result in a density of approximately 62,500 particles per square inch as compared with the current number of serrations capable of being inscribed of about 12 to about 36 per square inch.

Figure 22:
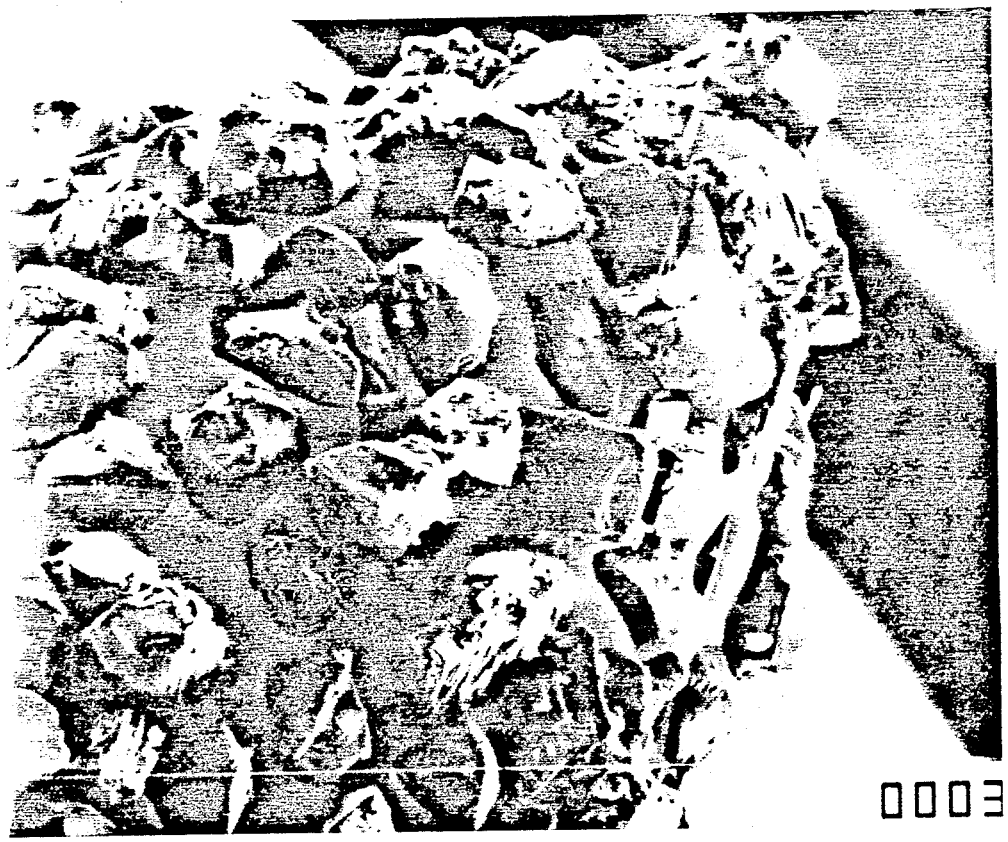
FIG. 22 is an electron-scanning microscopic photograph, taken at a magnification of 150×, of an engaging surface of the present invention.

Referring again to FIG. 22, electron-scanning microscopic photographs illustrate the increased number of contact points provided by the present invention. Since each individual diamond particles has an exterior surface including a myriad of points, the co-aptive contact points per square inch can be increased by approximately 500,000, depending upon the size of the grit used. As a result, the number of contact points may be increased to approximately 500,000 times that of current hemostats or needle-holders. FIG. 22 shows an enlarged view of a portion of the engaging surface 24 of the present invention at a magnification of 150×. The photograph best shows the regularity of the crystalline particles, in this case diamonds, the uniformity of the particle dispersion, and the leveling uniformity and smoothness of, in this case, the metallic matrix, with all of the discrete particles securely captured by and extending partially outward from the matrix.

There are a number of methods for single-layer attachment of crystalline, in one example diamond particles, available through high technology, state-of-the-art plating procedures. A few examples are contained in the following publications, the disclosures of which are hereby incorporated by reference:

ELECTROPLATING, by Frederick A. Lowenheim (McGraw-Hill, 1978);

ELECTROPLATING ENGINEERING HANDBOOK III, by Kenneth Graham Van Nostrand (Reinhold, 1971);

NICKEL PLATING, by R. Bruger (Robert Draper Ltd., 1970);

HEAVY DISPOSITION, by J. D. Greenwood, (Robert Draper Ltd. 1970):

MAKING DIAMOND TOOLS, by P. Daniel, (Industrial Diamond Review No. 27, Nov. 1967, Pg, 466-470):

NICKEL PLATED DIAMOND TOOLS, by D. A. Lindebeck and C. G. McAlonan Debeers Research, (Industrial Diamond Review, March 1974, Pgs. 84-88); and Various standard practice bulletins and procedures for preparation of materials and methods of plating, such as those available from the American Society for Testing and Materials, Philadelphia, Pa., e.g., ASTM B254-79, "Preparation of an Electroplating on Stainless Steel", effective Mar. 30, 1979; ASTM B242-54, "Preparation for High Carbon Steel for Electroplating", effective Sept. 15, 1954; ASTM B281-82, "Preparation of Copper and Copper-based Alloys for Electroplating and Conversion Coating", effective Sept. 24, 1982; ASTM B343-79, "Preparation of Nickel for Electroplating with Nickel", effective Jan. 26, 1979; and ASTM B183-79, "Preparation of Low Carbon Steel for Electroplating", effective Mar. 30, 1979. In addition, other various government publications concerning military specifications, e.g., electroplating deposited nickel, specification QQ-N-290, Class 1 (corrosion protection) or Class 2 (engineering plating to specified thickness and dimension); or sulfamate nickel specification no. QQ-N-290, Class 2 AMS 2424, can provide those skilled in the art with the methodology of nickel-diamond electro-deposition.

A preferred method for fabricating the instruments of the invention is as follows:

A stainless steel instrument having blank surfaces on which the co-aptive surfaces are to be formed is placed in a holding jig and all but such surfaces masked with an appropriate material such as plating tape, stop-off lacquer, or shrink tubing. The exposed surfaces are then pretreated to remove grease, oil films, oxides or any other foreign material therefrom. This cleaning process may be achieved by electrolysis, immersion baths or combination of both. In addition, a "strike bath" may be included to insure an even coherent deposit during the initial stages of deposition. The techniques for cleaning steel surfaces are well known in the art and are described in ASTM Bulletins for the Preparation of Steel (ANSI/ASTMB183-79; B242-54; and B254-79) published by the American Society for Testing and Materials, Philadelphia, Pa.

Figure 23:
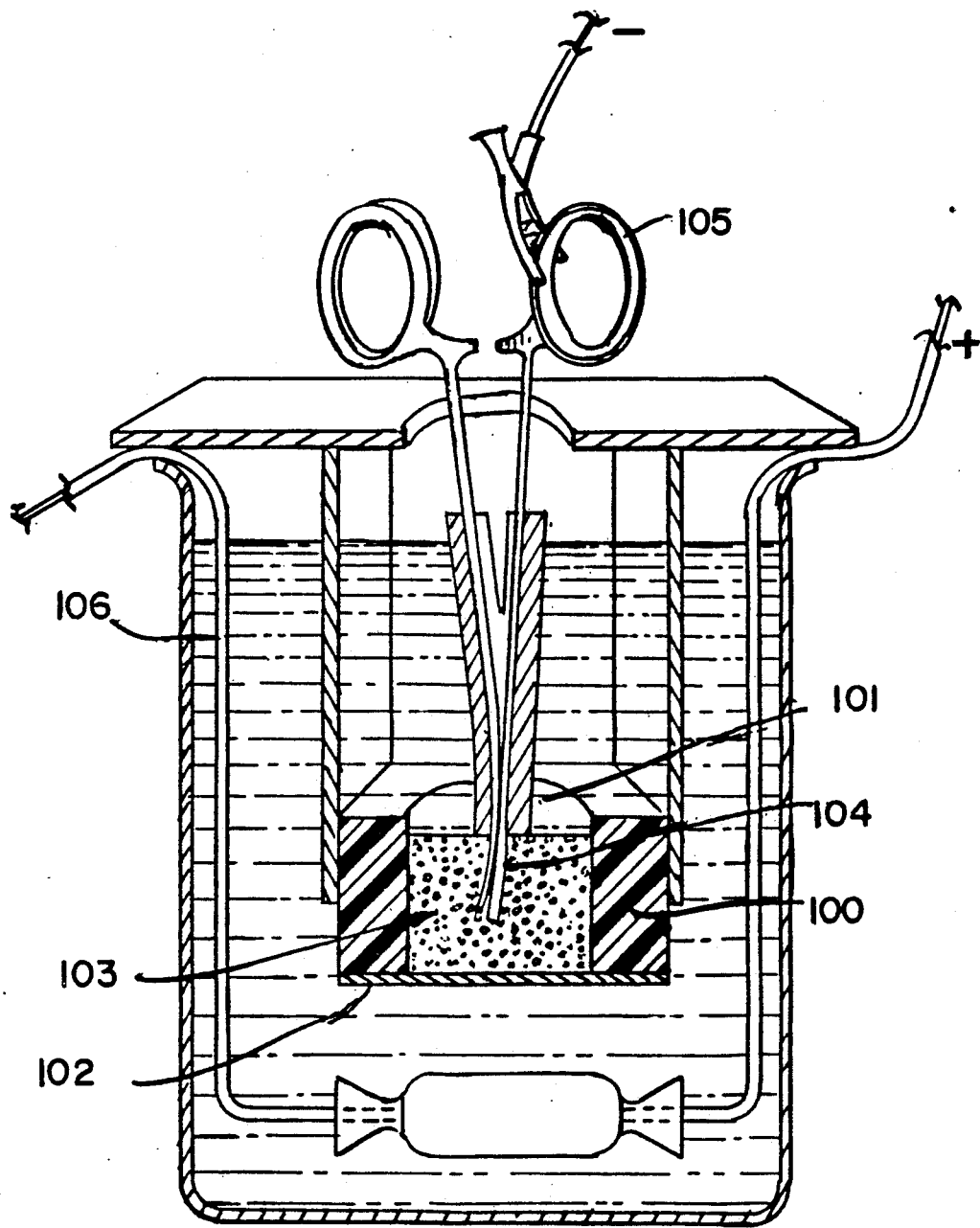
FIG. 23 is a schematic drawing illustrating apparatus which may be used in carrying out the method of the invention.

Commercially available natural diamond particles having a 100/120 grit (0.006"-0.005") are "tacked down" or "captured" on the pretreated surfaces in a sulfamate nickel plating bath. The thickness of the initial capture layer is preferably 10% of the average diameters of the diamond particles to ensure capture. Referring to FIG. 23, a fixture 100 is used of an inert plastic such as plexiglass having a through hole 101 larger than the instrument and having a taut permeable membrane 102 across one end, this membrane being of a material such as silk which will not pass the diamond particles. The cavity is filled with the diamond grit 103 and the surfaces 104 to be plated immersed in the grit. It is important that the surfaces which are to form the co-aptive surfaces be completely covered by the diamond particles without gaps or voids, with the particles in juxtaposition. To assure this end result, the diamond particles are tamped or vibrated either ultrasonically or manually, this vibrational energy being applied to the plastic fixture 100.

The fixture 100 in which the instrument 105 is mounted is lowered into an electrolytic sulfamate nickel bath 106 which can be obtained chemically from SELREX, a division of HOOKER CHEMICAL COMPANY. The tool can be placed in the bath either before or after the above indicated vibration of the particles. With an appropriate electrolytic current applied as indicated in FIG. 24, nickel ions are caused to migrate through the membrane and the diamond particles, depositing on the instrument surface and entrapped the particles to form a monolayer of diamond particles in a nickel matrix which is firmly adhered to the instrument surface. It is essential to form a proper co-aptive surface that the current density for the electrolytic bath, the time for plating, the temperature of the bath and the pH of the bath be accurately controlled. The current density and plating time are a function of the surface area of the instrument to be plated. It has been found that about 50% of the surface of the instrument is covered by diamond particles so that the apparent area to be covered is twice that of the conducting surface. This then must be considered in determining the current density and plating time. The pH of the solution must be controlled so that it is between 3.8 and 4.2 with an optimum value of 4.0, measured electrometically. The maintenance of the pH in this critical range is necessary to assure optimum capture of the particulate material providing proper tensile strength, hardness and elasticity of the nickel matrix.

After the plating has continued for sufficient time to fully capture the diamond particles and the instrument has been inspected for proper plating and particles coverage, the instrument is transferred to another electrolytic bath identical to the first (without diamond particles) so that the firm "trackdown" of the diamond particles is assured. In this second bath, the current density may be increased to increase plating speed. The plating is continued until the total depth of matrix is at least 50% of the average diameter of the diamond grit. A typical plating rate for a current density of 20 amperes per square foot is about 0.001 inches/hour. Using 100 mesh diamonds which have an average diameter of 0.0055 inches, the matrix should be about 0.003 inches thick to hold the diamond particles securely.

After the plating has been completed, the instrument is thoroughly washed in hot and cold flowing rinses to remove all traces of the plating bath and the instrument hot air dried and microscopically inspected to make sure it is within tolerances. The instrument can, if so desired for cosmetic reasons, be plated with a thin layer of chromium, gold or palladium after suitable activation of the nickel.

Additional methods for forming the co-aptive instruments of the present invention include the crystalline particles being melt-processed into thermoplastic instrument surfaces. If conductivity is critical, the plastic instrument can be metallized after production, by way of example, but not limited to, metallic vacuum deposition. While gold is preferred for vacuum deposition, other suitable materials, e.g., palladium or platinum, may be used. In addition, the incorporation of carbon fibers (e.g. graphite) or metal powders within the thermoplastic surfaces could provide the desired electroconductivity. The crystalline particles can also be evenly dispersed upon the instrument surface which is first coated with an adhesive. The adhesive can be cured by air, heat or ultraviolet radiation to ensure a positive encapsulation of the particles. Other methods for forming the improved engaging surface upon the substrate include, for example, other electrodeposition, electroformation, evaporation vapor-deposition, sintering, auto-catalytic deposition or fusion processes well-known to those skilled in the art.

One of the main considerations in the present invention is the incorporation of a multi-tip rough surface to engage the tissue in the manner of a hemostat or forceps. The use of randomly positioned, discrete, crystalline particles, e.g., diamond particles, partially embedded in a matrix greatly increases the number of contact points available to enhance the grip of the tissue between the engaging surfaces. The limitations due to the size of the inscribing instrument and to the morphology of narrow, sharp serrations are avoided. Incorporating this improved construction increases the gripping friction without having to resort to other conventional gripping surface configurations, e.g., those presently used by conventional Nelson, Allis or Adair forceps, which may puncture or tear the tissue grasped between the jaws. The partial embedding of numerous discrete particles upon the engaging surface, as opposed to serrations or cross-hatching of conventional co-aptive instruments, increases the number of contact points approximately 500,000× greater than current hemostats, forceps or needle-holders as earlier described.

Since the crystalline particles, e.g., diamonds, randomly adhere to the engaging surface, there are no well-defined grooves, increasing the co-aptive instrument's grip of generally rectilinear items. This random disposition of contact points upon the engaging surface and the increased number of contact points reduces the tendency of a grasped rectilinear item, e.g., a needle, to roll about its central longitudinal axis when used during suturing.

As a result, the co-aptive instrument 10 provides an engaging surface that is extremely resistent to slippage under tension, which remains electrically conductive and inert, and is easily sterilized, reducing subsequent infection, if it is inadvertently left within the body. As a result, the co-aptive instrument 10 provides a means for firmly but delicately grasp material. The incorporation of this engaging surface 24 within the co-aptive instrument 10, provides an engaging surface which can be delicately machined to specific tolerances.

Indeed, the co-aptive instrument 10 of the present invention will expedite surgical procedures. The time normally lost while engaging surfaces will be reduced. Suturing procedures will proceed more quickly, since needle slippage or the rotation attendant with the use of conventional forceps or hemostats is reduced. The patient may suffer fewer injuries (or trauma) and less tissue damage, since an increased compressive force need not be exerted upon the tissue or other instrument being held between the co-aptive diamond jaws to increase grip.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A method for fabricating tissue grasping co-aptive surfaces on blank opposing surfaces of a surgical instrument comprising the steps of:
   thoroughly cleaning said blank surfaces to remove all foreign material therefrom;
   placing a diamond grit of hard crystalline particles into a cavity formed in a fixture of an inert material, said cavity having a membrane covering one end thereof, said membrane having a mesh size such that the grip particles cannot pass therethrough;
   immersing said blank surfaces in said grit and vibrating the particles so that they completely cover said surfaces;
   placing said fixture along with the surfaces of said instrument which are covered by said grit into an electrolytic sulfamate nickel bath with said surfaces being completely immersed in said bath;
   applying an electrolytic current to said bath to cause nickels ions to migrate through the membrane and the grit particles and deposit on the surface of the instrument, nickel matrices being formed on said surfaces in which said particles are entrapped and thus adhered to said surfaces,
   immersing said surfaces with the particles adhered thereto into a second bath of sulfamate nickel;
   applying an electrolytic current to said second bath to plate nickel on said surfaces until the depth of the matrices are at least 50% of the diameter of the diamond particles to firmly anchor said particles in said matrices; and
   thoroughly washing the instrument to remove all traces of the bath.

2. The method of claim 1 wherein the pH of the plating baths is between 3.8 and 4.2.

3. The method f claim 1 wherein the diamond particles are natural and of 100/120 grit, the matrix being plated to a depth of 0.002–0.003 inches.

4. The method of claim 1 wherein said surgical instrument is of stainless steel.

* * * * *